United States Patent
Longo

(10) Patent No.: US 9,580,737 B2
(45) Date of Patent: Feb. 28, 2017

(54) PROTEIN ISOLATION

(71) Applicant: Michael Longo, Whittier, CA (US)

(72) Inventor: Michael Longo, Whittier, CA (US)

(73) Assignee: IDEA TREE, LLC, City of Industry, CA (US)

( * ) Notice: Subject to any disclaimer, the term of this patent is extended or adjusted under 35 U.S.C. 154(b) by 0 days.

(21) Appl. No.: 14/497,314

(22) Filed: Sep. 25, 2014

(65) Prior Publication Data

US 2015/0087023 A1    Mar. 26, 2015

(51) Int. Cl.
*C12P 21/00* (2006.01)
*C07K 14/245* (2006.01)

(52) U.S. Cl.
CPC .......... *C12P 21/00* (2013.01); *C07K 14/245* (2013.01); *C07K 2319/22* (2013.01)

(58) Field of Classification Search
None
See application file for complete search history.

(56) References Cited

PUBLICATIONS

Terpe, Appl Microbiol Biotechnol, 2003, vol. 60 pp. 523-533.*
Calloni et al., Cell reports, 2012, vol. 1 pp. 251-264.*

* cited by examiner

*Primary Examiner* — Mindy G Brown
(74) *Attorney, Agent, or Firm* — Kleinberg & Lerner, LLP; Marvin H. Kleinberg; Marshall A. Lerner

(57) ABSTRACT

A general method and strains of bacteria are described by means where the endogeneous DNAK protein or homolog of the DNAK protein is tagged with a recognizable amino acid sequence and that through this tag, DNAK may be efficiently removed, and as such, recombinant protein purification may be greatly improved both in yield and purity with simplified purification steps that remove the DNAK and reduced cost, waste accumulation and labor, and the isolated recombinant protein will significantly benefit research and therapeutics in its application.

8 Claims, 7 Drawing Sheets

Figure 3.

SEQUENCE LISTING

<160> NUMBER OF SEQ ID NOS: 59

<210> SEQ ID NO 1
<211> LENGTH: 3363
<212> TYPE: DNA
<213> ORGANISM: Escherichia coli

<400> SEQUENCE: 1

| | | | | | | |
|---|---|---|---|---|---|---|
| tttgcctgcg | ccgtgcagca | cagcatcagg | ctaatcgcca | ggctggcgga | aatcgtaaaa | 60 |
| acggatttca | taaggattct | cttagtggga | agaggtaggg | ggatgaatac | ccactagttt | 120 |
| actgctgata | aagagaagat | tcaggcacgt | aatcttttct | ttttattaca | atttttttgat | 180 |
| gaatgccttg | gctgcgattc | attctttata | tgaataaaat | tgctgtcaat | tttacgtctt | 240 |
| gtcctgccat | atcgcgaaat | ttctgcgcaa | aagcacaaaa | aattttttgca | tctcccccctt | 300 |
| gatgacgtgg | tttacgaccc | catttagtag | tcaaccgcag | tgagtgagtc | tgcaaaaaaa | 360 |
| tgaaattggg | cagttgaaac | cagacgtttc | gcccctatta | cagactcaca | accacatgat | 420 |
| gaccgaatat | atagtggaga | cgtttagatg | ggtaaaataa | ttggtatcga | cctgggtact | 480 |
| accaactctt | gtgtagcgat | tatggatggc | accactcctc | gcgtgctgga | aacgccgaa | 540 |
| ggcgatcgca | ccacgccttc | tatcattgcc | tatacccagg | atggtgaaac | tctagttggt | 600 |
| cagccggcta | aacgtcaggc | agtgacgaac | ccgcaaaaca | ctctgtttgc | gattaaacgc | 660 |
| ctgattggtc | gccgcttcca | ggacgaagaa | gtacagcgtg | atgtttccat | catgccgttc | 720 |
| aaaattattg | ctgctgataa | cggcgacgca | tgggtcgaag | ttaaaggcca | gaaaatggca | 780 |
| ccgccgcaga | tttctgctga | agtgctgaaa | aaaatgaaga | aaaccgctga | agattacctg | 840 |
| ggtgaaccgg | taactgaagc | tgttatcacc | gtaccggcat | actttaacga | tgctcagcgt | 900 |
| caggcaacca | aagacgcagg | ccgtatcgct | ggtctggaag | taaaacgtat | catcaacgaa | 960 |
| ccgaccgcag | ctgcgctggc | ttacggtctg | gacaaaggca | ctggcaaccg | tactatcgcg | 1020 |
| gtttatgacc | tgggtggtgg | tactttcgat | atttctatta | tcgaaatcga | cgaagttgac | 1080 |
| ggcgaaaaaa | ccttcgaagt | tctggcaacc | aacggtgata | cccacctggg | gggtgaagac | 1140 |
| ttcgacagcc | gtctgatcaa | ctatctggtt | gaagaattca | agaaagatca | gggcattgac | 1200 |
| ctgcgcaacg | atccgctggc | aatgcagcgc | ctgaaagaag | cggcagaaaa | agcgaaaatc | 1260 |
| gaactgtctt | ccgctcagca | gaccgacgtt | aacctgccat | acatcactgc | agacgcgacc | 1320 |
| ggtccgaaac | acatgaacat | caaagtgact | cgtgcgaaac | tggaaagcct | ggttgaagat | 1380 |
| ctggtaaacc | gttccattga | gccgctgaaa | gttgcactgc | aggacgctgg | cctgtccgta | 1440 |
| tctgatatcg | acgacgttat | cctcgttggt | ggtcagactc | gtatgccaat | ggttcagaag | 1500 |
| aaagttgctg | agttctttgg | taaagagccg | cgtaaagacg | ttaacccgga | cgaagctgta | 1560 |
| gcaatcggtg | ctgctgttca | gggtggtgtt | ctgactggtg | acgtaaaaga | cgtactgctg | 1620 |
| ctggacgtta | ccccgctgtc | tctgggtatc | gaaaccatgg | gcggtgtgat | gacgacgctg | 1680 |
| atcgcgaaaa | acaccactat | cccgaccaag | cacagccagg | tgttctctac | cgctgaagac | 1740 |
| aaccagtctg | cggtaaccat | ccatgtgctg | cagggtgaac | gtaaacgtgc | ggctgataac | 1800 |
| aaatctctgg | gtcagttcaa | cctagatggt | atcaacccgg | caccgcgcgg | catgccgcag | 1860 |
| atcgaagtta | ccttcgatat | cgatgctgac | ggtatcctgc | acgtttccgc | gaaagataaa | 1920 |
| aacagcggta | aagagcagaa | gatcaccatc | aaggcttctt | ctggtctgaa | cgaagatgaa | 1980 |
| atccagaaaa | tggtacgcga | cgcagaagct | aacgccgaag | ctgaccgtaa | gtttgaagag | 2040 |
| ctggtacaga | ctcgcaacca | gggcgaccat | ctgctgcaca | gcacccgtaa | gcaggttgaa | 2100 |

```
gaagcaggcg acaaactgcc ggctgacgac aaaactgcta tcgagtctgc gctgactgca    2160
ctggaaactg ctctgaaagg tgaagacaaa gccgctatcg aagcgaaaat gcaggaactg    2220
gcacaggttt cccagaaact gatggaaatc gcccagcagc aacatgccca gcagcagact    2280
gccggtgctg atgcttctgc aaacaacgcg aaagatgacg atgttgtcga cgctgaattt    2340
gaagaagtca agacaaaaa ataatcgccc tataaacggg taattatact gacacgggcg    2400
aaggggaatt cctctccgc ccgtgcattc atctaggggc aatttaaaaa agatggctaa    2460
gcaagattat tacgagattt taggcgtttc caaaacagcg gaagagcgtg aaatcagaaa    2520
ggcctacaaa cgcctggcca tgaaatacca cccggaccgt aaccagggtg acaaagaggc    2580
cgaggcgaaa tttaaagaga tcaaggaagc ttatgaagtt ctgaccgact cgcaaaaacg    2640
tgcggcatac gatcagtatg gtcatgctgc gtttgagcaa ggtggcatgg gcggcggcgg    2700
ttttggcggc ggcgcagact tcagcgatat ttttggtgac gttttcggcg atattttttgg    2760 cggcggacgt ggtcgtcaac gtgcggcgcg cggtgctgat ttacgctata acatggagct    2820
caccctcgaa gaagctgtac gtggcgtgac caaagagatc cgcattccga ctctggaaga    2880
gtgtgacgtt tgccacggta gcggtgcaaa accaggtaca cagccgcaga cttgtccgac    2940
ctgtcatggt tctggtcagg tgcagatgcg ccagggattc ttcgctgtac agcagacctg    3000
tccacactgt cagggccgcg gtacgctgat caaagatccg tgcaacaaat gtcatggtca    3060
tggtcgtgtt gagcgcagca aaacgctgtc cgttaaaatc ccggcagggg tggacactgg    3120
agaccgcatc cgtcttgcgg gcgaaggtga agcgggcgag catggcgcac cggcaggcga    3180
tctgtacgtt caggttcagg ttaaacagca cccgattttc gagcgtgaag caacaacct     3240 gtattgcgaa gtcccgatca acttcgctat ggcggcgctg ggtggcgaaa tcgaagtacc    3300 gaccccttgat ggtcgcgtca aactgaaagt gcctggcgaa acccagaccg gtaagctatt    3360
ccg                                                                   3363

<210> SEQ ID NO 2
<211> LENGTH: 35
<212> TYPE: DNA
<213> ORGANISM: Artificial Sequence
<220> FEATURE:
<223> OTHER INFORMATION: Outer Forward Primer I for DnaK in E. coli

<400> SEQUENCE: 2
caaggcccat ggtggtctga acgaagatga aatcc                                35

<210> SEQ ID NO 3
<211> LENGTH: 54
<212> TYPE: DNA
<213> ORGANISM: Artificial Sequence
<220> FEATURE:
<223> OTHER INFORMATION: Inter Reverse primer for Dnak in E. coli

<400> SEQUENCE: 3
cgacacaatt gttatttttc gaactgagct cgattttttg tctttgactt cttc           54

<210> SEQ ID NO 4
<211> LENGTH: 54
<212> TYPE: DNA
<213> ORGANISM: Artificial Sequence
<220> FEATURE:
<223> OTHER INFORMATION: Inter Fwd primer

<400> SEQUENCE: 4
gttcgaaaaa taacaattgt gtcgccctat aaacgggtaa ttatactgac acgg           54
```

```
<210> SEQ ID NO 5
<211> LENGTH: 47
<212> TYPE: DNA
<213> ORGANISM: Artificial Sequence
<220> FEATURE:
<223> OTHER INFORMATION: Outer rev primer

<400> SEQUENCE: 5
tgacgacccc tagggccgcc aaaaatatcg ccgaaaacgt caccaaa          47

<210> SEQ ID NO 6
<211> LENGTH: 844
<212> TYPE: DNA
<213> ORGANISM: Artificial Sequence
<220> FEATURE:
<223> OTHER INFORMATION: PCR amplified sequence from E. coli with added
      restriction sites

<400> SEQUENCE: 6
tggtctgaac gaagatgaaa tccagaaaat ggtacgcgac gcagaagcta acgccgaagc    60
tgaccgtaag tttgaagagc tggtacagac tcgcaaccag ggcgaccatc tgctgcacag   120
cacccgtaag caggttgaag aagcaggcga caaactgccg gctgacgaca aaactgctat   180
cgagtctgcg ctgactgcac tggaaactgc tctgaaaggt gaagacaaag ccgctatcga   240
agcgaaaatg caggaactgg cacaggtttc ccagaaactg atggaaatcg cccagcagca   300
acatgcccag cagcagactg ccggtgctga tgcttctgca aacaacgcga agatgacga    360 tgttgtcgac gctgaatttg aagaagtcaa agacaaaaaa tcgagctcag ttcgaaaaat   420
aacaattgtg tcgccctata acgggtaat tatactgaca cgggcgaagg ggaatttcct    480
ctccgcccgt gcattcatct aggggcaatt taaaaaagat ggctaagcaa gattattacg   540
agattttagg cgtttccaaa acagcggaag agcgtgaaat cagaaaggcc tacaaacgcc   600
tggccatgaa ataccacccg gaccgtaacc agggtgacaa agaggccgag gcgaaattta   660
aagagatcaa ggaagcttat gaagttctga ccgactcgca aaaacgtgcg gcatacgatc   720
agtatggtca tgctgcgttt gagcaaggtg gcatgggcgg cggcggtttt ggcggcggcg   780
cagacttcag cgatattttt ggtgacgttt tcggcgatat ttttggcggc ggacgtggtc   840
gtca                                                                844

<210> SEQ ID NO 7
<211> LENGTH: 96
<212> TYPE: DNA
<213> ORGANISM: Artificial Sequence
<220> FEATURE:
<223> OTHER INFORMATION: Upper Oligo (sense)

<400> SEQUENCE: 7
caagcgcttg gagccacccg cagttcgaga aaggtggagg ttccggaggt ggatcgggag    60
gtggatcgtg gagccacccg cagttcgaaa aataat                              96

<210> SEQ ID NO 8
<211> LENGTH: 104
<212> TYPE: DNA
<213> ORGANISM: Artificial Sequence
<220> FEATURE:
<223> OTHER INFORMATION: Lower oligo (antisense)

<400> SEQUENCE: 8
aattattatt ttcgaactg cgggtggctc cacgatccac ctcccgatcc acctccggaa    60
cctccacctt tctcgaactg cgggtggctc caagcgcttg agct                    104
```

<210> SEQ ID NO 9
<211> LENGTH: 924
<212> TYPE: DNA
<213> ORGANISM: Artificial Sequence
<220> FEATURE:
<223> OTHER INFORMATION: With strep sequence ligated in

<400> SEQUENCE: 9

```
tggtctgaac gaagatgaaa tccagaaaat ggtacgcgac gcagaagcta acgccgaagc    60
tgaccgtaag tttgaagagc tggtacagac tcgcaaccag ggcgaccatc tgctgcacag   120
cacccgtaag caggttgaag aagcaggcga caaactgccg gctgacgaca aaactgctat   180
cgagtctgcg ctgactgcac tggaaactgc tctgaaaggt gaagacaaag ccgctatcga   240
agcgaaaatg caggaactgg cacaggtttc ccagaaactg atggaaatcg cccagcagca   300
acatgcccag cagcagactg ccggtgctga tgcttctgca aacaacgcga agatgacga    360
tgttgtcgac gctgaatttg aagaagtcaa agacaaaaaa tcgagctcaa gcgcttggag   420
ccacccgcag ttcgagaaag gtggaggttc cggaggtgga tcgggaggtg gatcgtggag   480
ccacccgcag ttcgaaaaat aataattgtg tcgccctata acgggtaat tatactgaca    540
cgggcgaagg ggaatttcct ctccgcccgt gcattcatct aggggcaatt taaaaaagat   600
ggctaagcaa gattattacg agattttagg cgtttccaaa acagcggaag agcgtgaaat   660
cagaaaggcc tacaaacgcc tggccatgaa ataccacccg gaccgtaacc agggtgacaa   720
agaggccgag gcgaaattta aagagatcaa ggaagcttat gaagttctga ccgactcgca   780
aaaacgtgcg gcatacgatc agtatggtca tgctgcgttt gagcaaggtg gcatgggcgg   840
cggcggtttt ggcggcggcg cagacttcag cgatattttt ggtgacgttt tcggcgatat   900
ttttggcggc ggacgtggtc gtca                                          924
```

<210> SEQ ID NO 10
<211> LENGTH: 303
<212> TYPE: PRT
<213> ORGANISM: Artificial Sequence
<220> FEATURE:
<223> OTHER INFORMATION: Translated Sequence C

<400> SEQUENCE: 10

```
Gly Leu Asn Glu Asp Glu Ile Gln Lys Met Val Arg Asp Ala Glu Ala
1               5                  10                  15

Asn Ala Glu Ala Asp Arg Lys Phe Glu Glu Leu Val Gln Thr Arg Asn
            20                  25                  30

Gln Gly Asp His Leu Leu His Ser Thr Arg Lys Gln Val Glu Glu Ala
        35                  40                  45

Gly Asp Lys Leu Pro Ala Asp Asp Lys Thr Ala Ile Glu Ser Ala Leu
    50                  55                  60

Thr Ala Leu Glu Thr Ala Leu Lys Gly Glu Asp Lys Ala Ala Ile Glu
65                  70                  75                  80

Ala Lys Met Gln Glu Leu Ala Gln Val Ser Gln Lys Leu Met Glu Ile
                85                  90                  95

Ala Gln Gln Gln His Ala Gln Gln Thr Ala Gly Ala Asp Ala Ser
            100                 105                 110

Ala Asn Asn Ala Lys Asp Asp Val Val Asp Ala Glu Phe Glu Glu
        115                 120                 125
```

```
Val Lys Asp Lys Lys Ser Ser Ser Ala Trp Ser His Pro Gln Phe
    130                 135                 140

Glu Lys Gly Gly Gly Ser Gly Gly Gly Ser Gly Gly Ser Trp Ser
145                 150                 155                 160

His Pro Gln Phe Glu Lys Leu Cys Arg Pro Ile Asn Gly Leu Tyr His
                165                 170                 175

Gly Arg Arg Gly Ile Ser Ser Pro Val His Ser Ser Arg Gly Asn
            180                 185                 190

Leu Lys Lys Met Ala Lys Gln Asp Tyr Tyr Glu Ile Leu Gly Val Ser
        195                 200                 205

Lys Thr Ala Glu Glu Arg Glu Ile Arg Lys Ala Tyr Lys Arg Leu Ala
    210                 215                 220

Met Lys Tyr His Pro Asp Arg Asn Gln Gly Asp Lys Glu Ala Glu Ala
225                 230                 235                 240

Lys Phe Lys Glu Ile Lys Glu Ala Tyr Glu Val Leu Thr Asp Ser Gln
                245                 250                 255

Lys Arg Ala Ala Tyr Asp Gln Tyr Gly His Ala Ala Phe Glu Gln Gly
            260                 265                 270

Gly Met Gly Gly Gly Phe Gly Gly Ala Asp Phe Ser Asp Ile
        275                 280                 285

Phe Gly Asp Val Phe Gly Asp Ile Phe Gly Gly Arg Gly Arg
    290                 295                 300
```

<210> SEQ ID NO 11
<211> LENGTH: 185
<212> TYPE: PRT
<213> ORGANISM: Artificial Sequence
<220> FEATURE:
<223> OTHER INFORMATION: DnaK with a modified C-terminus

<400> SEQUENCE: 11

```
Ser Ala Lys Asp Lys Asn Ser Gly Lys Glu Gln Lys Ile Thr Ile Lys
1               5                   10                  15

Ala Ser Ser Gly Leu Asn Glu Asp Glu Ile Gln Lys Met Val Arg Asp
                20                  25                  30

Ala Glu Ala Asn Ala Glu Ala Asp Arg Lys Phe Glu Glu Leu Val Gln
            35                  40                  45

Thr Arg Asn Gln Gly Asp His Leu Leu His Ser Thr Arg Lys Gln Val
    50                  55                  60

Glu Glu Ala Gly Asp Lys Leu Pro Ala Asp Asp Lys Thr Ala Ile Glu
65                  70                  75                  80

Ser Ala Leu Thr Ala Leu Glu Thr Ala Leu Lys Gly Glu Asp Lys Ala
                85                  90                  95

Ala Ile Glu Ala Lys Met Gln Glu Leu Ala Gln Val Ser Gln Lys Leu
            100                 105                 110

Met Glu Ile Ala Gln Gln Gln His Ala Gln Gln Thr Ala Gly Ala
    115                 120                 125

Asp Ala Ser Ala Asn Asn Ala Lys Asp Asp Val Val Asp Ala Glu
130                 135                 140

Phe Glu Glu Val Lys Asp Lys Lys Ser Ser Ser Ala Trp Ser His
145                 150                 155                 160

Pro Gln Phe Glu Lys Gly Gly Gly Ser Gly Gly Gly Ser Gly Gly Gly
                165                 170                 175

Ser Trp Ser His Pro Gln Phe Glu Lys
            180                 185
```

```
<210> SEQ ID NO 12
<211> LENGTH: 638
<212> TYPE: PRT
<213> ORGANISM: Escherichia coli

<400> SEQUENCE: 12

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
    370                 375                 380
```

Asp Val Lys Asp Val Leu Leu Asp Val Thr Pro Leu Ser Leu Gly
385                 390                 395                 400

Ile Glu Thr Met Gly Gly Val Met Thr Thr Leu Ile Ala Lys Asn Thr
            405                 410                 415

Thr Ile Pro Thr Lys His Ser Gln Val Phe Ser Thr Ala Glu Asp Asn
        420                 425                 430

Gln Ser Ala Val Thr Ile His Val Leu Gln Gly Glu Arg Lys Arg Ala
    435                 440                 445

Ala Asp Asn Lys Ser Leu Gly Gln Phe Asn Leu Asp Gly Ile Asn Pro
450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
            485                 490                 495

Gln Lys Ile Thr Ile Lys Ala Ser Ser Gly Leu Asn Glu Asp Glu Ile
        500                 505                 510

Gln Lys Met Val Arg Asp Ala Glu Ala Asn Ala Glu Ala Asp Arg Lys
    515                 520                 525

Phe Glu Glu Leu Val Gln Thr Arg Asn Gln Gly Asp His Leu Leu His
530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
            565                 570                 575

Lys Gly Glu Asp Lys Ala Ala Ile Glu Ala Lys Met Gln Glu Leu Ala
        580                 585                 590

Gln Val Ser Gln Lys Leu Met Glu Ile Ala Gln Gln His Ala Gln
    595                 600                 605

Gln Gln Thr Ala Gly Ala Asp Ala Ser Ala Asn Asn Ala Lys Asp Asp
610                 615                 620

Asp Val Val Asp Ala Glu Phe Glu Glu Val Lys Asp Lys Lys
625                 630                 635

<210> SEQ ID NO 13
<211> LENGTH: 671
<212> TYPE: PRT
<213> ORGANISM: Artificial Sequence
<220> FEATURE:
<223> OTHER INFORMATION: DNAK (E. coli) with a double Strep Tag fused
      to the C-terminus

<400> SEQUENCE: 13

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
            85                  90                  95

Asp Asn Gly Asp Ala Trp Val Glu Val Lys Gly Gln Lys Met Ala Pro
        100                 105                 110

Pro Gln Ile Ser Ala Glu Val Leu Lys Lys Met Lys Lys Thr Ala Glu
            115                 120                 125

Asp Tyr Leu Gly Glu Pro Val Thr Glu Ala Val Ile Thr Val Pro Ala
130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
            165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
            195                 200                 205

Glu Val Asp Gly Glu Lys Thr Phe Glu Val Leu Ala Thr Asn Gly Asp
            210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
            245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
            275                 280                 285

Asp Ala Thr Gly Pro Lys His Met Asn Ile Lys Val Thr Arg Ala Lys
            290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
            325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
            355                 360                 365

Glu Ala Val Ala Ile Gly Ala Ala Val Gln Gly Gly Val Leu Thr Gly
            370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
            405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
            435                 440                 445

Ala Asp Asn Lys Ser Leu Gly Gln Phe Asn Leu Asp Gly Ile Asn Pro
            450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
            485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
            515                 520                 525

```
Phe Glu Glu Leu Val Gln Thr Arg Asn Gln Gly Asp His Leu Leu His
            530                 535                 540
Ser Thr Arg Lys Gln Val Glu Glu Ala Gly Asp Lys Leu Pro Ala Asp
545                 550                 555                 560
Asp Lys Thr Ala Ile Glu Ser Ala Leu Thr Ala Leu Glu Thr Ala Leu
                565                 570                 575
Lys Gly Glu Asp Lys Ala Ala Ile Glu Ala Lys Met Gln Glu Leu Ala
            580                 585                 590
Gln Val Ser Gln Lys Leu Met Glu Ile Ala Gln Gln Gln His Ala Gln
            595                 600                 605
Gln Gln Thr Ala Gly Ala Asp Ala Ser Ala Asn Asn Ala Lys Asp Asp
            610                 615                 620
Asp Val Val Asp Ala Glu Phe Glu Glu Val Lys Asp Lys Lys Ser Ser
625                 630                 635                 640
Ser Ser Ala Trp Ser His Pro Gln Phe Glu Lys Gly Gly Ser Gly
                645                 650                 655
Gly Gly Ser Gly Gly Gly Ser Trp Ser His Pro Gln Phe Glu Lys
            660                 665                 670

<210> SEQ ID NO 14
<211> LENGTH: 9
<212> TYPE: PRT
<213> ORGANISM: Artificial Sequence
<220> FEATURE:
<223> OTHER INFORMATION: DNAK MASCOT Data Fragment 1

<400> SEQUENCE: 14

Lys Val Ala Glu Phe Phe Gly Lys Glu
1               5

<210> SEQ ID NO 15
<211> LENGTH: 9
<212> TYPE: PRT
<213> ORGANISM: Artificial Sequence
<220> FEATURE:
<223> OTHER INFORMATION: DNA MASCOT Data Fragment 2

<400> SEQUENCE: 15

Lys Asp Gln Gly Ile Asp Leu Arg Asn
1               5

<210> SEQ ID NO 16
<211> LENGTH: 10
<212> TYPE: PRT
<213> ORGANISM: Artificial Sequence
<220> FEATURE:
<223> OTHER INFORMATION: DNAK MASCOT Data Fragment 3

<400> SEQUENCE: 16

Arg Asn Asp Pro Leu Ala Met Gln Arg Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: DNAK MASCOT Data Fragment 4

<400> SEQUENCE: 17

Arg Phe Gln Asp Glu Glu Val Gln Arg Asp
1               5                   10
```

```
<210> SEQ ID NO 18
<211> LENGTH: 11
<212> TYPE: PRT
<213> ORGANISM: Artificial Sequence
<220> FEATURE:
<223> OTHER INFORMATION: DNAK MASCOT Data Fragment 5

<400> SEQUENCE: 18

Arg Lys Phe Glu Glu Leu Val Gln Ile Arg Asn
1               5                   10

<210> SEQ ID NO 19
<211> LENGTH: 12
<212> TYPE: PRT
<213> ORGANISM: Artificial Sequence
<220> FEATURE:
<223> OTHER INFORMATION: DNAK MASCOT Data Fragment 6

<400> SEQUENCE: 19

Lys Val Ala Glu Phe Phe Gly Lys Glu Pro Arg Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: DNAK MASCOT Data Fragment 7

<400> SEQUENCE: 20

Arg Leu Ile Asn Tyr Leu Val Glu Glu Phe Lys Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: DNAK MASCOT Data Fragment 8

<400> SEQUENCE: 21

Arg Asn Gln Gly Asp His Leu Leu His Ser Thr Arg Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: DNAK MASCOT Data Fragment 9

<400> SEQUENCE: 22

Lys Met Ala Pro Pro Gln Ile Ser Ala Glu Val Leu Lys Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: DNAK MASCOT Data Fragment 10

<400> SEQUENCE: 23

Lys Leu Glu Ser Leu Val Glu Asp Leu Val Asn Arg Ser
1               5                   10
```

```
<210> SEQ ID NO 24
<211> LENGTH: 13
<212> TYPE: PRT
<213> ORGANISM: Artificial Sequence
<220> FEATURE:
<223> OTHER INFORMATION: DNAK MASCOT Data Fragment 11

<400> SEQUENCE: 24

Arg Leu Ile Asn Tyr Leu Val Glu Glu Phe Lys Lys Asp
1               5                   10

<210> SEQ ID NO 25
<211> LENGTH: 15
<212> TYPE: PRT
<213> ORGANISM: Artificial Sequence
<220> FEATURE:
<223> OTHER INFORMATION: DNAK MASCOT Data Fragment 12

<400> SEQUENCE: 25

Arg Ala Lys Leu Glu Ser Leu Val Glu Asp Leu Val Asn Arg Ser
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: DNAK MASCOT Data Fragment 13

<400> SEQUENCE: 26

Lys Ile Ile Ala Ala Asp Asn Gly Asp Ala Trp Val Glu Val Lys Gly
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: DNAK MASCOT Data Fragment 14

<400> SEQUENCE: 27

Arg Gln Ala Val Thr Asn Pro Gln Asn Thr Leu Phe Ala Ile Lys Arg
1               5                   10                  15

Gln

<210> SEQ ID NO 28
<211> LENGTH: 16
<212> TYPE: PRT
<213> ORGANISM: Artificial Sequence
<220> FEATURE:
<223> OTHER INFORMATION: DNAK MASCOT Data Fragment 15

<400> SEQUENCE: 28

Arg Gln Ala Val Thr Asn Pro Gln Asn Thr Leu Phe Ala Ile Lys Arg
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: DNAK MASCOT Data Fragment 16
```

<400> SEQUENCE: 29

Lys Ser Leu Gly Gln Phe Asn Leu Asp Gly Ile Asn Pro Ala Pro Arg
1               5                   10                  15

Gly

<210> SEQ ID NO 30
<211> LENGTH: 18
<212> TYPE: PRT
<213> ORGANISM: Artificial Sequence
<220> FEATURE:
<223> OTHER INFORMATION: DNAK MASCOT Data Fragment 17

<400> SEQUENCE: 30

Arg Ile Ile Asn Glu Pro Thr Ala Ala Ala Leu Ala Tyr Gly Leu Asp
1               5                   10                  15

Lys Gly

<210> SEQ ID NO 31
<211> LENGTH: 19
<212> TYPE: PRT
<213> ORGANISM: Artificial Sequence
<220> FEATURE:
<223> OTHER INFORMATION: DNAK MASCOT Data Fragment 18

<400> SEQUENCE: 31

Lys Arg Ile Ile Asn Glu Pro Thr Ala Ala Ala Leu Ala Tyr Gly Leu
1               5                   10                  15

Asp Lys Gly

<210> SEQ ID NO 32
<211> LENGTH: 23
<212> TYPE: PRT
<213> ORGANISM: Artificial Sequence
<220> FEATURE:
<223> OTHER INFORMATION: DNAK MASCOT Data Fragment 19

<400> SEQUENCE: 32

Arg Thr Thr Pro Ser Ile Ile Ala Tyr Thr Gln Asp Gly Glu Thr Leu
1               5                   10                  15

Val Gly Gln Pro Ala Lys Arg
            20

<210> SEQ ID NO 33
<211> LENGTH: 21
<212> TYPE: PRT
<213> ORGANISM: Artificial Sequence
<220> FEATURE:
<223> OTHER INFORMATION: DNAK MASCOT Data Fragment 21

<400> SEQUENCE: 33

Lys Phe Glu Glu Leu Val Gln Thr Arg Asn Gln Gly Asp His Leu Leu
1               5                   10                  15

His Ser Thr Arg Lys
            20

<210> SEQ ID NO 34
<211> LENGTH: 23
<212> TYPE: PRT
<213> ORGANISM: Artificial Sequence
<220> FEATURE:
<223> OTHER INFORMATION: DNAK MASCOT Data Fragment 21

-continued

```
<400> SEQUENCE: 34

Lys Thr Phe Glu Val Leu Ala Thr Asn Gly Asp Thr His Leu Gly Gly
1               5                   10                  15

Glu Asp Phe Asp Ser Arg Leu
            20

<210> SEQ ID NO 35
<211> LENGTH: 24
<212> TYPE: PRT
<213> ORGANISM: Artificial Sequence
<220> FEATURE:
<223> OTHER INFORMATION: DNAK MASCOT Data Fragment 22

<400> SEQUENCE: 35

Lys Ile Ile Gly Ile Asp Leu Gly Thr Thr Asn Ser Cys Val Ala Ile
1               5                   10                  15

Met Asp Gly Thr Thr Pro Arg Val
            20

<210> SEQ ID NO 36
<211> LENGTH: 24
<212> TYPE: PRT
<213> ORGANISM: Artificial Sequence
<220> FEATURE:
<223> OTHER INFORMATION: DNAK MASCOT Data Fragment 23

<400> SEQUENCE: 36

Arg Thr Thr Pro Ser Ile Ile Ala Tyr Thr Gln Asp Gly Glu Thr Leu
1               5                   10                  15

Val Gly Gln Pro Ala Lys Arg Gln
            20

<210> SEQ ID NO 37
<211> LENGTH: 27
<212> TYPE: PRT
<213> ORGANISM: Artificial Sequence
<220> FEATURE:
<223> OTHER INFORMATION: DNAK MASCOT Data Fragment 24

<400> SEQUENCE: 37

Arg Lys Asp Val Asn Pro Asp Glu Ala Val Ala Ile Gly Ala Ala Val
1               5                   10                  15

Gln Gly Gly Val Leu Thr Gly Asp Val Lys Asp
            20                  25

<210> SEQ ID NO 38
<211> LENGTH: 26
<212> TYPE: PRT
<213> ORGANISM: Artificial Sequence
<220> FEATURE:
<223> OTHER INFORMATION: DNAK MASCOT Data Fragment 25

<400> SEQUENCE: 38

Lys Val Ala Leu Gln Asp Ala Gly Leu Ser Val Ser Asp Ile Asp Asp
1               5                   10                  15

Val Ile Leu Val Gly Gly Gln Thr Arg Met
            20                  25

<210> SEQ ID NO 39
<211> LENGTH: 26
<212> TYPE: PRT
<213> ORGANISM: Artificial Sequence
<220> FEATURE:
<223> OTHER INFORMATION: DNAK MASCOT Data Fragment 26
```

<400> SEQUENCE: 39

Lys Ile Glu Leu Ser Ser Ala Gln Gln Thr Asp Val Asn Leu Pro Tyr
1               5                   10                  15

Ile Thr Ala Asp Ala Thr Gly Pro Lys His
            20                  25

<210> SEQ ID NO 40
<211> LENGTH: 27
<212> TYPE: PRT
<213> ORGANISM: Artificial Sequence
<220> FEATURE:
<223> OTHER INFORMATION: DNAK MASCOT Data Fragment 27

<400> SEQUENCE: 40

Lys Leu Met Glu Ile Ala Gln Gln Gln His Ala Gln Gln Gln Thr Ala
1               5                   10                  15

Gly Ala Asp Ala Ser Ala Asn Asn Ala Lys Asp
            20                  25

<210> SEQ ID NO 41
<211> LENGTH: 26
<212> TYPE: PRT
<213> ORGANISM: Artificial Sequence
<220> FEATURE:
<223> OTHER INFORMATION: DNAK MASCOT Data Fragment 28

<400> SEQUENCE: 41

Met Gly Lys Ile Ile Gly Ile Asp Leu Gly Thr Thr Asn Ser Cys Val
1               5                   10                  15

Ala Ile Met Asp Gly Thr Thr Pro Arg Val
            20                  25

<210> SEQ ID NO 42
<211> LENGTH: 28
<212> TYPE: PRT
<213> ORGANISM: Artificial Sequence
<220> FEATURE:
<223> OTHER INFORMATION: DNAK MASCOT Data Fragment 29

<400> SEQUENCE: 42

Lys Ala Lys Ile Glu Leu Ser Ser Ala Gln Gln Thr Asp Val Asn Leu
1               5                   10                  15

Pro Tyr Ile Thr Ala Asp Ala Thr Gly Pro Lys His
            20                  25

<210> SEQ ID NO 43
<211> LENGTH: 28
<212> TYPE: PRT
<213> ORGANISM: Artificial Sequence
<220> FEATURE:
<223> OTHER INFORMATION: DNAK MASCOT Data Fragment 29

<400> SEQUENCE: 43

Lys Thr Ala Glu Asp Tyr Leu Gly Glu Pro Val Thr Glu Ala Val Ile
1               5                   10                  15

Thr Val Pro Ala Tyr Phe Asn Asp Ala Gln Arg Gln
            20                  25

<210> SEQ ID NO 44
<211> LENGTH: 29
<212> TYPE: PRT
<213> ORGANISM: Artificial Sequence
<220> FEATURE:
<223> OTHER INFORMATION: DNAK MASCOT Data Fragment 31

```
<400> SEQUENCE: 44

Lys Lys Thr Ala Glu Asp Tyr Leu Gly Glu Pro Val Thr Glu Ala Val
1               5                   10                  15

Ile Thr Val Pro Ala Tyr Phe Asn Asp Ala Gln Arg Gln
            20                  25

<210> SEQ ID NO 45
<211> LENGTH: 40
<212> TYPE: PRT
<213> ORGANISM: Artificial Sequence
<220> FEATURE:
<223> OTHER INFORMATION: DNAK MASCOT Data Fragment 32

<400> SEQUENCE: 45

Lys Leu Met Glu Ile Ala Gln Gln Gln His Ala Gln Gln Gln Thr Ala
1               5                   10                  15

Gly Ala Asp Ala Ser Ala Asn Asn Ala Lys Asp Asp Val Val Asp
            20                  25                  30

Ala Glu Phe Glu Glu Val Lys Asp
            35                  40

<210> SEQ ID NO 46
<211> LENGTH: 197
<212> TYPE: PRT
<213> ORGANISM: Escherichia coli

<400> SEQUENCE: 46

Met Ser Ser Lys Glu Gln Lys Arg Pro Glu Gly Gln Ala Pro Glu Glu
1               5                   10                  15

Ile Ile Met Asp Gln His Glu Glu Ile Glu Ala Val Glu Pro Glu Ala
            20                  25                  30

Ser Ala Glu Gln Val Asp Pro Arg Asp Glu Lys Ile Ala Asn Leu Glu
            35                  40                  45

Ala Gln Leu Ala Glu Ala Gln Thr Arg Glu Arg Asp Gly Ile Leu Arg
        50                  55                  60

Val Lys Ala Glu Met Glu Asn Leu Arg Arg Arg Thr Glu Leu Asp Ile
65              70                  75                  80

Glu Lys Ala His Lys Phe Ala Leu Glu Lys Phe Ile Asn Glu Leu Leu
                85                  90                  95

Pro Val Ile Asp Ser Leu Asp Arg Ala Leu Glu Val Ala Asp Lys Ala
            100                 105                 110

Asn Pro Asp Met Ser Ala Met Val Glu Gly Ile Glu Leu Thr Leu Lys
        115                 120                 125

Ser Met Leu Asp Val Val Arg Lys Phe Gly Val Glu Val Ile Ala Glu
130                 135                 140

Thr Asn Val Pro Leu Asp Pro Asn Val His Gln Ala Ile Ala Met Val
145                 150                 155                 160

Glu Ser Asp Asp Val Ala Pro Gly Asn Val Leu Gly Ile Met Gln Lys
                165                 170                 175

Gly Tyr Thr Leu Asn Gly Arg Thr Ile Arg Ala Ala Met Val Thr Val
            180                 185                 190

Ala Lys Ala Lys Ala
        195

<210> SEQ ID NO 47
<211> LENGTH: 197
<212> TYPE: PRT
<213> ORGANISM: Escherichia coli
```

```
<400> SEQUENCE: 47

Met Ser Ser Lys Glu Gln Lys Thr Pro Glu Gly Gln Ala Pro Glu
1               5                   10                  15

Ile Ile Met Asp Gln His Glu Ile Glu Ala Val Glu Pro Glu Ala
            20                  25                  30

Ser Ala Glu Gln Val Asp Pro Arg Asp Glu Lys Val Ala Asn Leu Glu
        35                  40                  45

Ala Gln Leu Ala Glu Ala Gln Thr Arg Glu Arg Asp Gly Ile Leu Arg
    50                  55                  60

Val Lys Ala Glu Met Glu Asn Leu Arg Arg Arg Thr Glu Leu Asp Ile
65                  70                  75                  80

Glu Lys Ala His Lys Phe Ala Leu Glu Lys Phe Ile Asn Glu Leu Leu
                85                  90                  95

Pro Val Ile Asp Ser Leu Asp Arg Ala Leu Glu Val Ala Asp Lys Ala
            100                 105                 110

Asn Pro Asp Met Ser Ala Met Val Glu Gly Ile Glu Leu Thr Leu Lys
            115                 120                 125

Ser Met Leu Asp Val Val Arg Lys Phe Gly Val Glu Val Ile Ala Glu
    130                 135                 140

Thr Asn Val Pro Leu Asp Pro Asn Val His Gln Ala Ile Ala Met Val
145                 150                 155                 160

Glu Ser Asp Val Ala Pro Gly Asn Val Leu Gly Ile Met Gln Lys
                165                 170                 175

Gly Tyr Thr Leu Asn Gly Arg Thr Ile Arg Ala Ala Met Val Thr Val
            180                 185                 190

Ala Lys Ala Lys Ala
        195

<210> SEQ ID NO 48
<211> LENGTH: 9
<212> TYPE: PRT
<213> ORGANISM: Artificial Sequence
<220> FEATURE:
<223> OTHER INFORMATION: GRPE MASCOT Data Fragment 1

<400> SEQUENCE: 48

Lys Ser Met Leu Asp Val Val Arg Lys
1               5

<210> SEQ ID NO 49
<211> LENGTH: 9
<212> TYPE: PRT
<213> ORGANISM: Artificial Sequence
<220> FEATURE:
<223> OTHER INFORMATION: GRPE MASCOT Data Fragment 2

<400> SEQUENCE: 49

Lys Ser Met Leu Asp Val Val Arg Lys
1               5

<210> SEQ ID NO 50
<211> LENGTH: 9
<212> TYPE: PRT
<213> ORGANISM: Artificial Sequence
<220> FEATURE:
<223> OTHER INFORMATION: GRPE MASCOT Data Fragment 3

<400> SEQUENCE: 50

Arg Glu Arg Asp Gly Ile Leu Arg Val
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: GRPE MASCOT Data Fragment 4

<400> SEQUENCE: 51

Lys Ala Glu Met Glu Asn Leu Arg Arg
1               5

<210> SEQ ID NO 52
<211> LENGTH: 10
<212> TYPE: PRT
<213> ORGANISM: Artificial Sequence
<220> FEATURE:
<223> OTHER INFORMATION: GRPE MASCOT Data Fragment 5

<400> SEQUENCE: 52

Arg Arg Thr Glu Leu Asp Ile Glu Lys Ala
1               5                   10

<210> SEQ ID NO 53
<211> LENGTH: 11
<212> TYPE: PRT
<213> ORGANISM: Artificial Sequence
<220> FEATURE:
<223> OTHER INFORMATION: GRPE MASCOT Data Fragment 6

<400> SEQUENCE: 53

Arg Val Lys Ala Glu Met Glu Asn Leu Arg Arg
1               5                   10

<210> SEQ ID NO 54
<211> LENGTH: 16
<212> TYPE: PRT
<213> ORGANISM: Artificial Sequence
<220> FEATURE:
<223> OTHER INFORMATION: GRPE MASCOT Data Fragment  7

<400> SEQUENCE: 54

Lys Ile Ala Asn Leu Glu Ala Gln Leu Ala Glu Ala Gln Thr Arg Glu
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: GRPE MASCOT Data Fragment 8

<400> SEQUENCE: 55

Lys Phe Ile Asn Glu Leu Leu Pro Val Ile Asp Ser Leu Asp Arg Ala
1               5                   10                  15

<210> SEQ ID NO 56
<211> LENGTH: 19
<212> TYPE: PRT
<213> ORGANISM: Artificial Sequence
<220> FEATURE:
<223> OTHER INFORMATION: GRPE MASCOT Data Fragment 9

<400> SEQUENCE: 56

Lys Ala Asn Pro Asp Met Ser Ala Met Val Glu Gly Ile Glu Leu Thr
1               5                   10                  15

Leu Lys Ser
```

```
<210> SEQ ID NO 57
<211> LENGTH: 35
<212> TYPE: PRT
<213> ORGANISM: Artificial Sequence
<220> FEATURE:
<223> OTHER INFORMATION: GRPE MASCOT Data Fragment 10

<400> SEQUENCE: 57

Lys Thr Pro Glu Gly Gln Ala Pro Glu Ile Ile Met Asp Gln His
1               5                   10                  15

Glu Glu Ile Glu Ala Val Glu Pro Glu Ala Ser Ala Glu Gln Val Asp
            20                  25                  30

Pro Arg Asp
        35

<210> SEQ ID NO 58
<211> LENGTH: 42
<212> TYPE: PRT
<213> ORGANISM: Artificial Sequence
<220> FEATURE:
<223> OTHER INFORMATION: GRPE MASCOT Data Fragment 11

<400> SEQUENCE: 58

Lys Phe Gly Val Glu Val Ile Ala Glu Thr Asn Val Pro Leu Asp Pro
1               5                   10                  15

Asn Val His Gln Ala Ile Ala Met Val Glu Ser Asp Asp Val Ala Pro
            20                  25                  30

Gly Asn Val Leu Gly Ile Met Gln Lys Gly
        35                  40

<210> SEQ ID NO 59
<211> LENGTH: 43
<212> TYPE: PRT
<213> ORGANISM: Artificial Sequence
<220> FEATURE:
<223> OTHER INFORMATION: GRPE MASCOT Data Fragment 12

<400> SEQUENCE: 59

Arg Lys Phe Gly Val Glu Val Ile Ala Glu Thr Asn Val Pro Leu Asp
1               5                   10                  15

Pro Asn Val His Gln Ala Ile Ala Met Val Glu Ser Asp Asp Val Ala
            20                  25                  30

Pro Gly Asn Val Leu Gly Ile Met Gln Lys Gly
        35                  40
```

PROTEIN ISOLATION

BACKGROUND OF THE INVENTION

1. Field of the Invention

The present invention relates to methods for isolation of recombinant proteins, and namely methods that involve the removal of DNAK during the isolation procedure.

2. General Background and State of the Art

Obtaining substantial amounts of pure protein is essential in innumerable biological studies and indispensable to the biochemical characterization of proteins. The ease of growth, well-characterized genetics, and the large number of tools for gene expression has long made *Escherichia coli* (*E. Coli*) the organism of choice for protein overproduction.

DNAK is an abundant protein (about 1% of the total protein of *E. coli*) that interacts with a wide range of newly synthesized polypeptides whereby it acts as a chaperone. Chaperone proteins assist in the proper folding of newly expressed proteins and assembly into oligomers and thus prevent protein aggregation through interaction. DNAK binding to other proteins occurs when DNAK is bound to ADP, and release these proteins when bound to ATP. DNAK is also a required factor to disaggregate preformed protein aggregates, and it participates in the degradation of damaged proteins through protease specific channels.

While important for protein production, DNAK contamination presents a significant problem in protein purification. DNAK is able to bind to many proteins that are not endogenous to the bacterial host strain. Moreover, DNAK contamination may prevent the separation of recombinant fusion protein production, impair analysis of unfolding-refolding experiments, and cause strong antigenic responses in rats and rabbits even when the chaperone is present in trace amounts, which thereby affects antibody production.

Some recombinant protein isolation methods utilize *E. coli* DNAK deletion strains in order to eliminate DNAK contamination, but only when DNAK is not required to improve the solubility and the quality of the isolated recombinant proteins. Still, these deletions strains have narrower ranges of permissive temperatures for growth and exhibit multiple cellular defects which may reduce the overall yield of recombinant protein as well as stability of the strain.

Other methods involving fusion protein production utilize software based algorithms that determine appropriate amino acids surrounding the putative DNAK binding site of the recombinant protein and alter the sequence in order to decrease putative affinity for DNAK. Upon purification of these fusion protein bound to resin, MgATP plus soluble denatured *E. coli* proteins are used to wash the protein prior to elution. However, such methods are effective in only a limited number of cases, and not generally for all fusion proteins. Also, they do not eliminate contamination of their isolated recombination proteins that inherently contain putative DNAK binding sites. In addition, reagents of this procedure agents are costly and some are not suitable for commercial or therapeutic use (e.g. glycerol).

Alternate methods employ co-chaperone proteins which bind to DNAK in any of the nucleotide bound states. The co-chaperone protein was histidine tagged at the N-terminus, and this fusion recombinant protein was isolated by a one-step purification with nickel affinity chromatography. Despite the ability to remove DNAK via this co-chaperone, the method does not completely eliminate the DNAK, and relies on the transformation of an additional recombinant protein which reduces cellular resources needed to express the target recombinant protein at higher levels.

INVENTION SUMMARY

The invention is a method to remove DNAK during a recombinant protein purification. The method requires the use of a bacterial strain, commonly used for recombinant protein production, which is able to express a tagged DNAK. The bacterial strain may be *E. coli*. The protein tag may be incorporated into the genomic copy of the DNAK gene, resulting in a strain which produces the tagged DNAK endogenously. The strain may be a mutant strain wherein the endogenous DNAK has been deleted and the tagged DNAK is expressed from an introduced vector. The tag may be added to DNAK or a homolog of DNAK with the similar function as DNAK. The tag may be a histidine tag, myc tag or any equivalent tags wherein the tag is effective in the removal of the tagged protein when used with a resin based solid or liquid phase method or any other purification techniques that employ the use of tag for protein isolation.

The presence of DNAK is important for optimal replication of the bacterial culture which in turn allows for greater expression and yield of the target recombinant protein. The nucleotide sequence encoding the protein tag may be inserted into any region of the DNAK sequence that does not affect the function of DNAK and therefore, does not impair bacterial growth.

The tagged DNAK bacterial strain will first be transformed with the vector of the target recombinant protein. After the transformed bacterial culture has been incubated to the optimal level of growth, the cellular extract may be collected by standard means of isolation. The cellular extract may then be applied to resin containing the tag's ligand directed toward the tagged DNAK. When used in chromatography, the DNAK and any DNAK-bound protein remains bound to the resin, and the eluate contains the target recombinant protein. Further isolation of the target recombinant proteins maybe employed. In alternate methods, tagged DNAK may be removed after the target recombinant protein has been initially isolated. Other methods may include subsequent rounds of tagged DNAK isolation.

The novel features which are characteristic of the invention, both as to structure and method of operation thereof, together with further objects and advantages thereof, will be understood from the following description, considered in connection with the accompanying drawings, in which the preferred embodiment of the invention is illustrated by way of example. It is to be expressly understood, however, that the drawings are for the purpose of illustration and description only, and they are not intended as a definition of the limits of the invention.

DESCRIPTION OF THE DRAWINGS

FIG. 3. The MASCOT data of Band 1 shown in FIG. 2 wherein SEQ ID No. 12 is the amino acid sequence of DNAK protein, SEQ ID No. 13 is the amino acid sequence of DNAK protein with a double strep tag fused to the C-terminus, and SEQ ID Nos. 14-45 are the MASCOT peptide fragments of DNAK protein.

Figure 1:
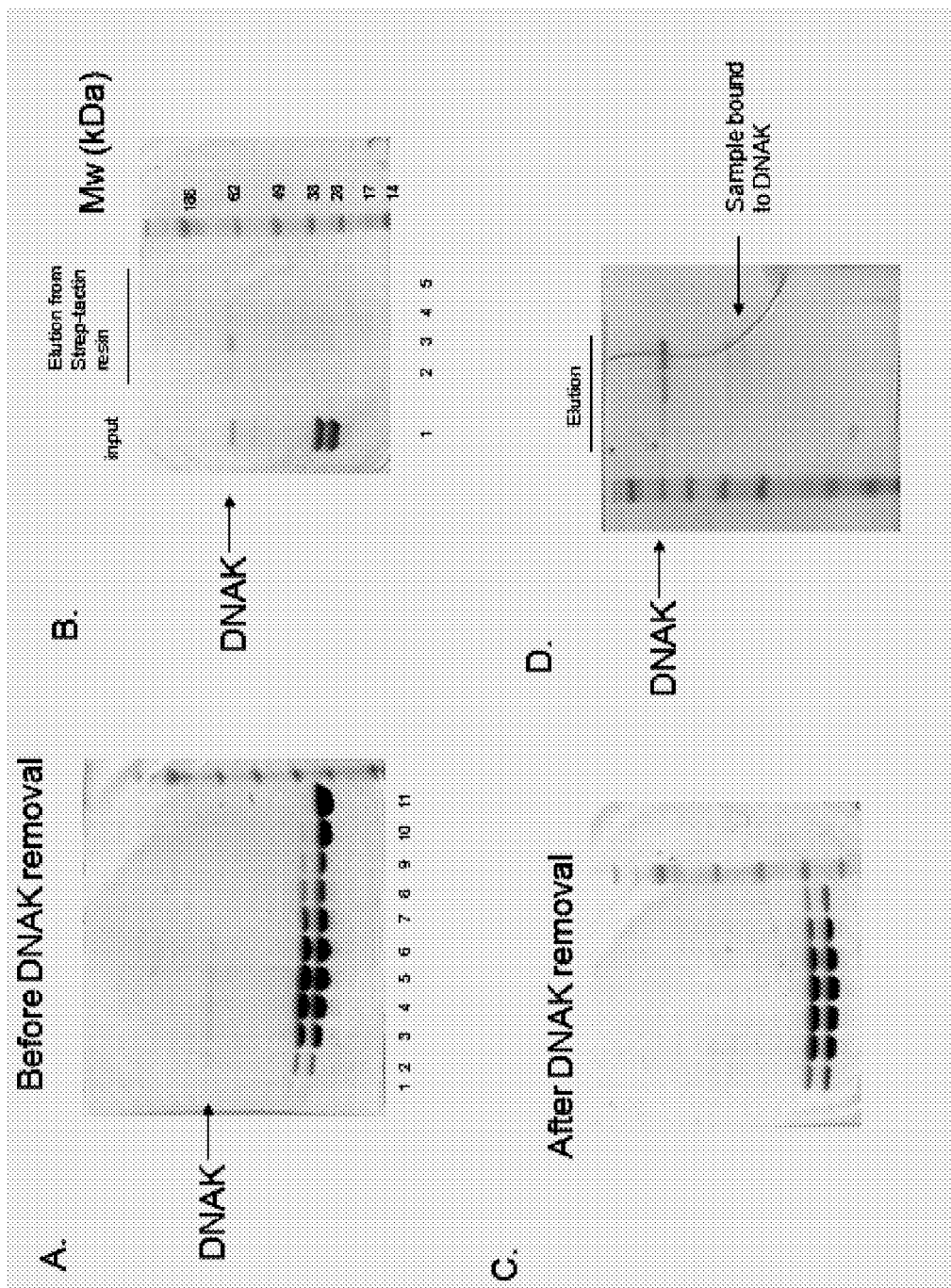
FIG. 1. A-B. The exemplary gels that show the efficacy of DNAK removal.

DETAILED DESCRIPTION OF THE INVENTION (i) Definitions

The following definitions, unless otherwise stated, apply to all aspects and embodiments of the present application.

The term "DNAK" refers to an *E. coli* protein that plays an essential role in the initiation of phage lambda DNA replication, where it acts in an ATP-dependent fashion with the DnaJ protein to release lambda O and P proteins from the preprimosomal complex. DnaK is also involved in chromosomal DNA replication, possibly through an analogous interaction with the DnaA protein. Also the protein participates actively in the response to hyperosmotic shock.

The term "GrpE" refers to an *E. coli* protein that participates actively in the response to hyperosmotic and heat shock by preventing the aggregation of stress-denatured proteins, in association with DnaK and GrpE. It is the nucleotide exchange factor for DnaK and may function as a thermosensor. Unfolded proteins bind initially to DnaJ; upon interaction with the DnaJ-bound protein, DnaK hydrolyzes its bound ATP, resulting in the formation of a stable complex. GrpE releases ADP from DnaK; ATP binding to DnaK triggers the release of the substrate protein, thus completing the reaction cycle. Several rounds of ATP-dependent interactions between DnaJ, DnaK and GrpE are required for fully efficient folding.

A "plasmid" is a vector that refers to an independently replicating circular double-stranded piece of DNA. The plasmid may contain an origin of replication such as the *E. coli* oriC, an selectable antibiotic resistance gene conferring resistance to but not limited to β-lactam, macrolide, and aminoglycosides antibiotics, a promoter sequence under expression control, and a multiple cloning site containing restriction sites.

The plasmid may be an "expression plasmid". Expression plasmids allow for the expression of a cloned gene. An expression plasmid contains an inducible promoter region that allows for the regulation and induction of gene expression of a gene cloned into the plasmid's multiple cloning site, a ribosomal binding site, a start codon, a stop codon, and a termination of transcription sequence.

The term "promoter sequence" is a region of DNA either upstream or downstream from the site of initiation of transcription of a gene. As used herein, a bacterial promoter includes necessary consensus sequences of TTGACA at the −35 and a Pribnow box TATAAT sequence at the −10 position upstream of the start of transcription, and may also contain an UP element upstream of the −35 region.

"BL21-(DE3) is an *E. coli* strain that is chemically competent for transformation and protein expression. The strain may express proteins under the control the T7 promoter. The strain is deficient in protease Lon and OmpT.

The term "transformation" refers to a process of introducing exogenous genetic material into a bacterium by methods employing membrane permeability via chemical or electrical means. Performing a transformation involves adding genetic material, such as a plasmid, to an aliquot of competent bacterial cells, such as *E. coli*, and allowing the mixture to incubate on ice. The bacterial cells are then either electroporated or placed at 42° C. for approximately 1 minute and then returned to incubate on ice. The bacterial cells are then grown on an agar plate overnight until colonies are visible. The agar plate may contain antibiotic or nutrient conditions for colony selection.

The term "transfection" refers is the process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. "Transduction" is often used to describe virus-mediated DNA transfer. *Nature Methods* 2, 875-883 (2005)

The term "homologous sequence" refers to an amino acid or nucleotide sequence that is at least 70% to 99% homologous to a corresponding reference sequence. Sequences that are 90% identical have no more than one different amino acid per 10 amino acids in the reference sequence. The percentage of homology between two or more sequences may be identified using a homology algorithm of Smith and Waterman (1970) Adv. Appl. Math 2:482c, Needleman and Wunsch (1970) J. Mol. Biol. 48:433, or Pearson and Lipman (1988) Proc. Natl. Sci. 85:2444. The methods of sequence alignment are known to those in the art. A computer based program employing the mentioned or alternative sequence comparison algorithms may be used such as BLAST as described in The NCBI Handbook (2002) or ClustalOmega as described in Sievers et. al. Mol. Sys. Bio. 7:539 (2011).

"Homologous recombination" refers to a type of genetic recombination in which nucleotide sequences are exchanged between two similar or identical molecules of DNA. It is most widely used by cells to accurately repair harmful breaks that occur on both strands of DNA, known as double-strand breaks. Although homologous recombination varies widely among different organisms and cell types, most forms involve the same basic steps. After a double-strand break occurs, sections of DNA around the 5' ends of the break are cut away in a process called resection. In the strand invasion step that follows, an overhanging 3' end of the broken DNA molecule then "invades" a similar or identical DNA molecule that is not broken. After strand invasion, the further sequence of events may follow either of two main pathways discussed below (see Models); the DSBR (double-strand break repair) pathway or the SDSA (synthesis-dependent strand annealing) pathway. Homologous recombination is conserved across all three domains of life as well as viruses, suggesting that it is a nearly universal biological mechanism. Alberts, B et al (2002). "Chapter 5: DNA Replication, Repair, and Recombination"

"Recombinant" DNA or protein is used to refer to DNA molecules formed by laboratory methods of genetic recombination (such as molecular cloning) to bring together genetic material from multiple sources, creating sequences that would not otherwise be found in biological organisms or used to refer to the proteins that are encoded by the recombinant DNA. Recombinant DNA are sometimes called chimeric DNA.

"Restriction Endonucleases" refer to enzymes that cut DNA at or near specific recognition nucleotide sequences known as restriction sites. Roberts R J (November 1976). "Restriction endonucleases". *CRC Crit. Rev. Biochem.* 4 (2): 123-64.

The term "amplification" refers to the act of mass replication of a genetic sequence. Amplification of a genetic sequence may be performed by PCR using primers that hybridize to flanking ends of a genetic sequence of interest. Amplification of a genetic sequence may also be performed in vivo by transforming bacteria with a plasmid or transfecting a host cell with a virus that carries the recombinant genetic sequence of interest.

The term "protein expression" refers to the production of protein within a host cell such as a bacteria, yeast, plant, or animal cell. A vector carrying the coding sequence for a recombinant protein under the control of a promoter, such as an expression plasmid, is inserted into a host cell. The promoter controlling the expression of the recombinant gene is then induced and the protein encoded by the recombinant gene is produced within the host cell.

The term "protein coding sequence" refers to a portion of a gene that codes for a polypeptide. The coding sequence is located between an ATG initiation of translation codon and the location of a TAG, TAA, or TGA termination of translation codon. Typical to eukaryotic genes, the coding sequence may include the "exons" of a gene, which is the sequence of a gene that is transcribed and translated into a polypeptide, and may exclude the "introns" of a gene, which is the sequence of a gene that is transcribed but not translated into a polypeptide.

The term "protein purification" refers to a process of purifying a protein and may employ any technique used to separate and isolate a protein of interest to a satisfactory level of purity. Protein purification exploits a protein's various properties such as size, charge, binding affinity, and biological activity. Liquid column chromatography is commonly used in protein purification where a cell lysate containing an expressed protein is passed over a "resin" with particular binding affinity for the protein of interest. A resin is a compound or a polymer with chemical properties that supports the purification of proteins via ion exchange, hydrophobic interaction, size exclusion, reverse phase, or affinity tag chromatography. A protein may also be purified by non-chromatographic techniques such as through the electroporation of protein from an excised piece of a polyacrylamide gel that contained a protein sample of interest.

The term "MALDI" refers to matrix-assisted laser desorption ionization which is a mass spectrometry technique used to analyze compounds, and biomolecules such as polypeptides and proteins, by determining their molecular masses. A protein sample is first prepared for MALDI by enzymatic digestion with a protease such as trypsin. The sample is then chemically coupled to a matrix and then introduced into the mass spectrometer. A pulsed laser beam targets the sample which results in desorption and ionization of the polypeptide from a solid to a gas phase. The vaporized ions are accelerated in an electric field towards a detector. Peptide fragments are then identified based on their mass-to-charge ratio via peptide mass fingerprinting or tandem mass spectrometry. The peptide masses are displayed as a list of molecular weight peaks which are then compared to a database of known peptide masses such as that of Swissprot allowing for a statistical identification of the original protein sample.

As used here, the term "MASCOT" refers to algorithm called MASCOT (Matrix Sciences) which is a search engine that is used for the identification and characterization of mass spectrometry protein data. The probalistic scoring depends on which of the matched proteins has the lowest probability of occurring by chance and is thus returned with the most significant match. A protein score of 85 or above (which corresponds to a $p<0.05$) is considered to be significant.

A "protein tag" refers to an amino acid sequence within a recombinant protein that provides new characteristics to the recombinant protein that assist in protein purification, identification, or activity based on the tag's characteristics and affinity. A protein tag may provide a novel enzymatic property to the recombinant protein such as a biotin tag, or a tag may provide a means of protein identification such as with fluorescence tags encoding for green fluorescent protein or red fluorescent protein. Protein tags may be added onto the N- or C-terminus of a protein. A common protein tag used in protein purification is a poly-His tag where a series of approximately six histidine amino acid residues are added which enables the protein to bind to protein purification matrices chelated to metal ions such as nickel or cobalt. Other tags commonly used in protein purification include Strep tag, chitin binding protein, maltose binding protein, glutathione-S-transferase, and FLAG-tag. Tags such as "epitope tags" may also confer the protein to have an affinity towards an antibody. Common antibody epitope tags include the V5-tag, Myc-tag, and HA-tag.

The terms "fusion protein" or "fused protein" refer to a protein that is coded by a single gene and the single gene is made up of coding sequences that originally coded for at least two or more separate proteins. A fusion protein may retain the functional domains of the two or more separate proteins. Part of the coding sequence for a fusion protein may code for an epitope tag. As described herein for the antibody like protein, a fusion protein may also contain sequences that code for a variety of proteins having vary functional roles based on its application. "polypeptides"

"Chromatography" is the collective term for a set of laboratory techniques for the separation of mixtures. The mixture is dissolved in a fluid called the mobile phase, which carries it through a structure holding another material called the stationary phase. The stationary phase may be referred to as a "resin". The various constituents of the mixture travel at different speeds, causing them to separate. The separation is based on differential partitioning between the mobile and stationary phases. Subtle differences in a compound's partition coefficient result in differential retention on the stationary phase and thus changing the separation.

Chromatography may be preparative or analytical. The purpose of preparative chromatography is to separate the components of a mixture for more advanced use (and is thus a form of purification). Analytical chromatography is done normally with smaller amounts of material and is for measuring the relative proportions of analytes in a mixture. The two are not mutually exclusive.

Size-exclusion chromatography or column (SEC) is also known as gel permeation chromatography (GPC) or gel filtration chromatography and separates molecules according to their size (or more accurately according to their hydrodynamic diameter or hydrodynamic volume). Smaller molecules are able to enter the pores of the media and, therefore, molecules are trapped and removed from the flow of the mobile phase. The average residence time in the pores depends upon the effective size of the analyte molecules. However, molecules that are larger than the average pore size of the packing are excluded and thus suffer essentially no retention; such species are the first to be eluted. It is generally a low-resolution chromatography technique and thus it is often reserved for the final, "polishing" step of a purification. It is also useful for determining the tertiary structure and quaternary structure of purified proteins, especially since it can be carried out under native solution conditions.

"Affinity chromatography" is a method of separating biochemical mixtures based on a highly specific interaction such as that between antigen and antibody, enzyme and substrate, or receptor and ligand. The term "column" may be used instead coupled with an explanation of the type of resin that is bound In molecular cloning, a "vector" is a DNA molecule used as a vehicle to artificially carry foreign genetic material into another cell, where it can be replicated and/or expressed. A vector containing foreign DNA is termed recombinant DNA. The four major types of vectors are plasmids, viral vectors, cosmids, and artificial chromosomes. Common to all engineered vectors are an origin of replication, a multicloning site, and a selectable marker.

The term Flippase recognition target "FRT" refers to the DNA sequence that is recognized by the enzyme called flippase which is responsible in part for homologous recombination. The 34 bp minimal FRT site sequence has the sequence "5'GAAGTTCCTATTCtctagaaaGtATAG-GAACTTC3'" for which flippase (Flp) binds to both 13-bp 5'-GAAGTTCCTATTC-3' arms flanking the 8 bp spacer, i.e. the site-specific recombination (region of crossover) in reverse orientation. FRT-mediated cleavage occurs just ahead from the asymmetric 8 bp core region (5' tctagaaa3') on the top strand and behind this sequence on the bottom strand. Several variant FRT sites exist, but recombination can usually occur only between two identical FRTs but generally not among non-identical ("heterospecific") FRTs. Zhu X D, Sadowski P D (1995). Zhu X D, Sadowski P D (1995). "Many available constructs include an additional arm sequences (5'-GAAGTTCCTATTCC-3') one base pair away from the upstream element and in the same orientation: "5' GAAGTTCCTATTCcGAAGTTCCTATTCtctagaaaGtATAGGAACTTC3'". This segment is dispensable for excision but essential for integration, including Recombinase-mediated cassette exchange.

Cleavage-dependent Ligation by the FLP Recombinase". Journal of Biological Chemistry 270 (39): 23044-54 Schlake T, Bode J (1994). "Use of mutated FLP recognition target (FRT) sites for the exchange of expression cassettes at defined chromosomal loci". Biochemistry 33 (43): 12746-12751

(ii) Polypeptide Sequences and Agents of the Application

Precise alterations were made in the genome of E. coli using the method of Link et al., 1997. Integrations are based on the pKO plasmids, pMH9 and pTOF24 (Merlin et al. 2002). These plasmids have the following features: chloramphenicol resistance gene, temperature sensitive OR1 with functionality at 30° C., but not 37-42° C., and the sacB gene, which renders cells sensitive to the presence of sucrose in growth media. An exemplary embodiment of the sequence of DNAK inserted into the pKO plasmid is in SEQ ID. 1.

An 800 bp region of homology to the E. coli genome is cloned at the restriction endonuclease sites of PstI and SalI of the pKO plasmid. The 800 bp region may be constructed using crossover PCR. The 800 bp DNA will contain additional alterations such as the tag encoding nucleotide sequences. Any such alterations will have 400 bp of homology flanking on either side of the location of the tag encoding nucleotide sequence. Alterations may also include adding unique restriction sites.

In an exemplary embodiment, the primers that may be used to amplify the tagged DNAK gene are depicted in SEQ ID. 2 & 3. It is understood by one with the ordinary skill of the art that other primers and locations of the tags and sites of homologous recombination maybe used to amplify the tagged DNAK gene.

The amplified DNAK sequence modified with a tag was inserted between two FRT cassettes present within an expression vector.

In the present application, one embodiment of the tagged DNAK gene sequence may contain an amino acid Strep-tag sequence (Trp-Ser-His-Pro-Gln-Phe-Glu-Lys) that was added to the C-terminus ended through DNA recombination as shown in SEQ ID. 9. A tag could also be added to the N-terminus region. In alternate embodiments, other tags such as a Flag-Tag, His-tag or Myc-tag or the like may also be used.

In the exemplary embodiment, the recombinant plasmids were transformed into recipient cells with chloramphenicol selection at 30° C. Recipient cells may be the BL21 (DE3) strain or the like. The DNAK strain was then allowed to homologously recombine with the E. Coli chromosome.

It is well known to those with ordinary skill in the art that other cells that contain homologs of DNAK could be genetically modified with the homolog containing a recognizable tag based on this exemplary embodiment. Primers may be constructed to amplify the DNAK homolog with the primers having the nucleotide sequence that encodes for the recognizable tag.

Colonies were grown on LB agar plates with chloramphenicol overnight at 42° C., and colonies were selected based on size. Selected colonies that demonstrated successful homologous recombination were then cross selected for growth on LB agar with 5% W/V sucrose at 37° C. Cross selected colonies were then simultaneously "patch tested" on LB agar containing 5% sucrose and on LB agar containing 5% sucrose and 5% chloramphenicol. Chloramphenicol sensitive colonies were screened by PCR and sequenced.

The modified DNAK or a homolog of a naturally occurring DNAK was isolated from the strain containing the homologously recombined tagged DNAK encoding gene to confirm a protein sequence through the use of the added tag. Chromatography or an equivalent method that targets the tag may be used to isolate the resultant protein.

Figure 2:
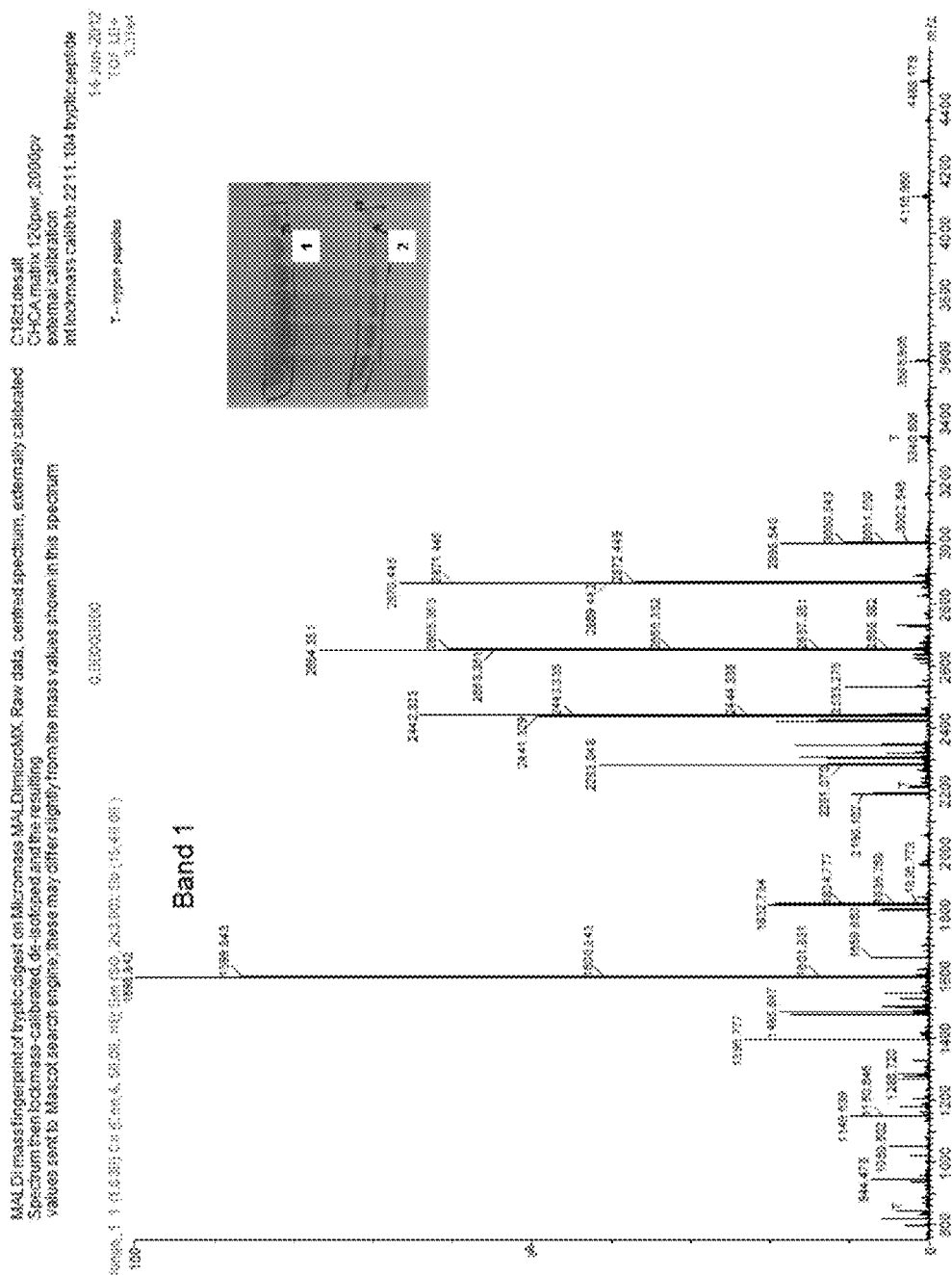
FIG. 2. The mass spectroscopy data used on the Band 1 as shown in the gel for the identification of the DNAK isolated band.

In the present embodiment, the bacterial lysate of the modified strain, BL21-DNAK-strep may be applied to a Strep-tactin resin column. The elute fractions may then be run on an SDS-protein gel as shown in FIG. 2. The Strep-tagged DNAK is shown with a molecular weight that corresponds to its estimated 72.4 kDa molecular weight. An additional lower molecular weight band was also observed and subsequent analysis revealed that the identity of the protein was Grp E, a commonly associated co-chaperone protein of DNAK. See the data below. (Sugimoto et al, Prot. Exp. And Pur., 60 31-36 (2008).

Figure 3:
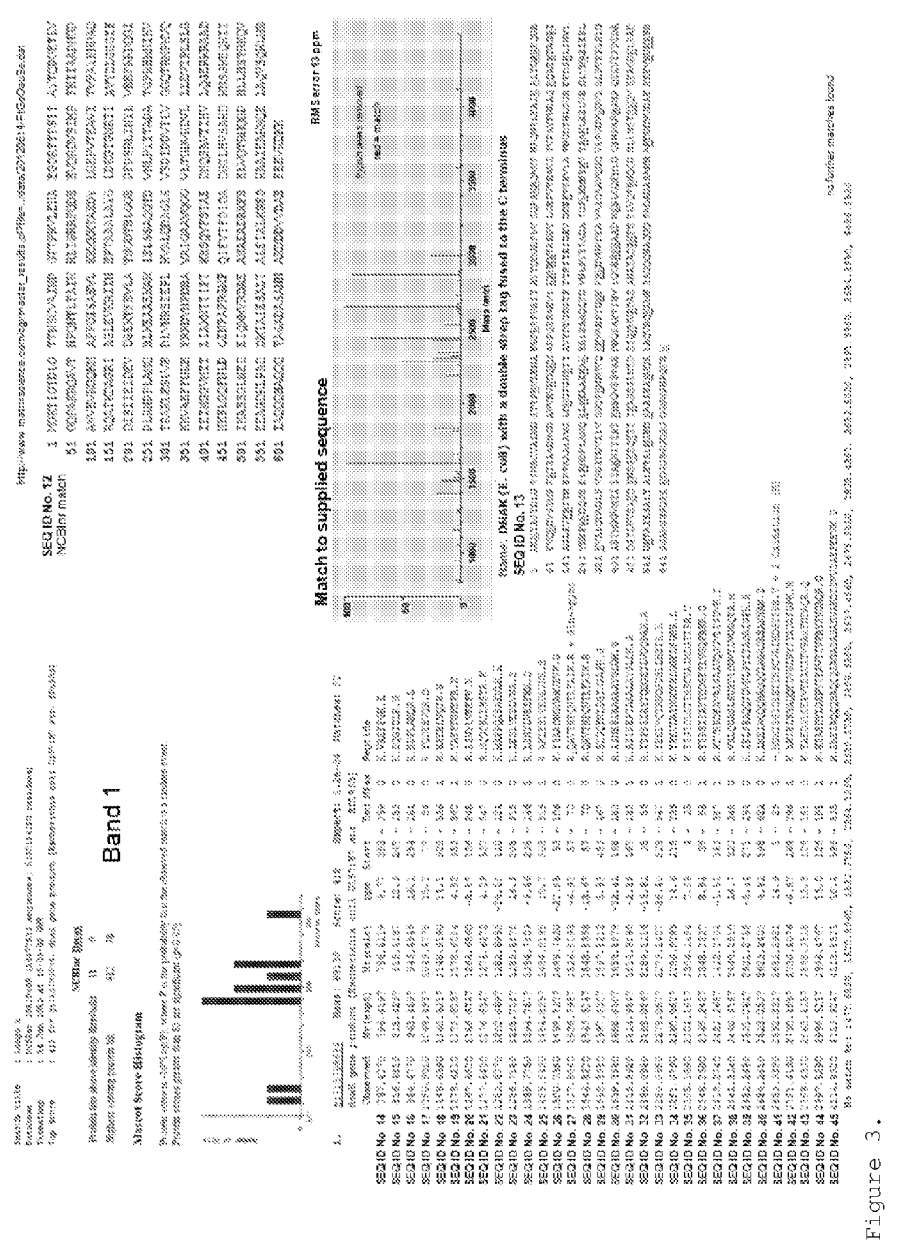

The bands may then be extracted from the gel and prepared for sequencing. The Strep-tagged DNAK may be partially digested and the resultant fragments isolated for the purposes of MALDI mass fingerprint analysis. In the present invention, the modified protein was subjected to a partial tryptic digestion. Digested fragments were then run through a Micromass MALDI microMX mass spectrometer. FIG. 2 shows the mass spectroscopy data of corresponding to FIG. 2 the gel of band 1 of the modified DNAK molecule. The data was then analyzed using the MASCOT algorithm which matched the mass spectrometer data to the DNAK gene product [*E. coli* 0157:H7 str. EDL9331] with the highest protein score of 412 as shown in FIG. 3.

Figure 4:
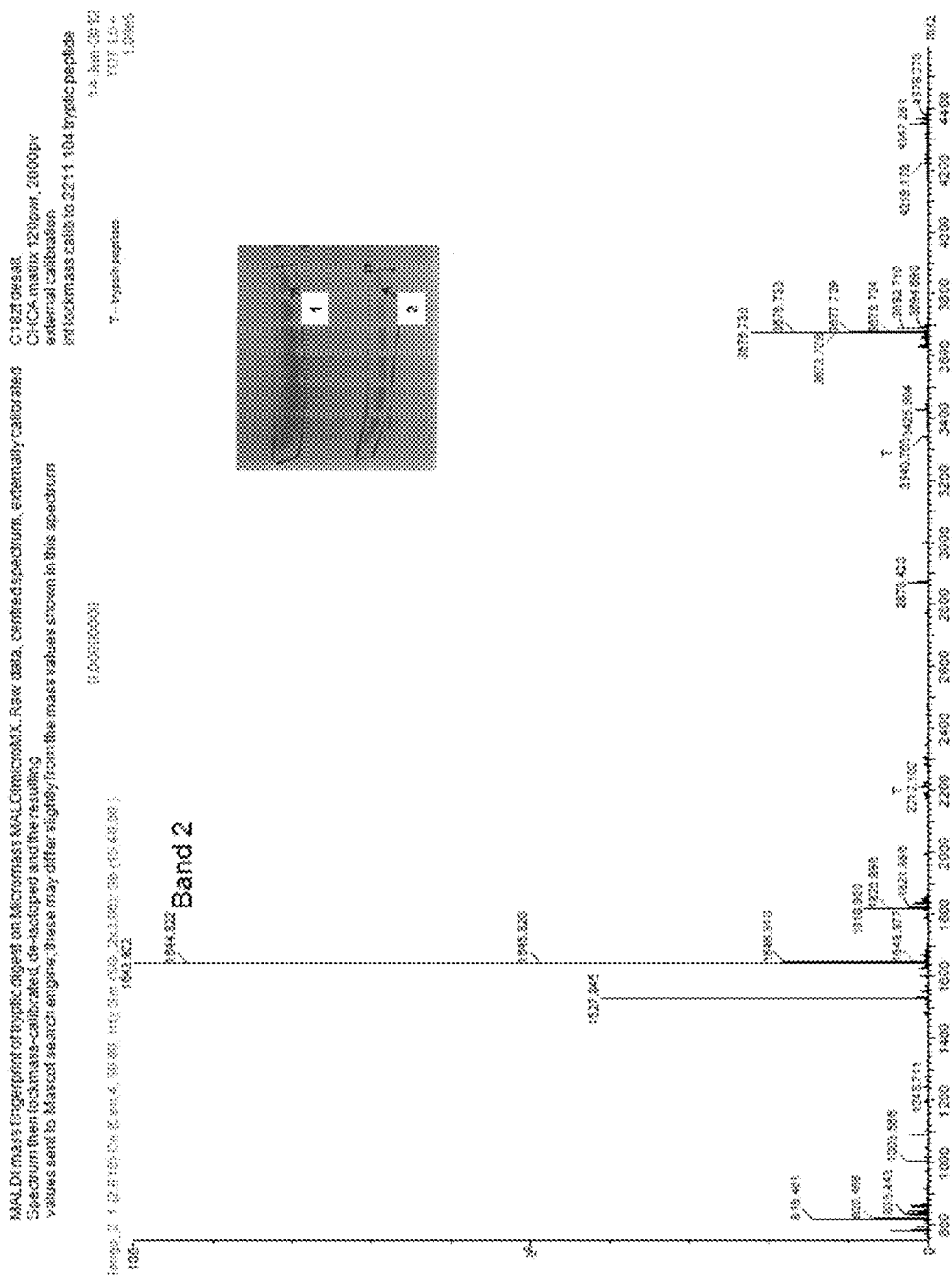
FIG. 4 The mass spectroscopy data used on the Band 2 as shown in the gel for the identification of the GRPE isolated band.

Band 2 from the SDS-PAGE of FIG. 4 was also analyzed under MALDI and had a MASCOT protein score of 185 for the grpE gene product [*E. coli* 0157:H7 str. EDL933]. The co-elution of GrpE with Strep-tagged DNAK demonstrates that the modified DNAK has retained its structural and functional confirmation as it is capable of binding and co-eluting with GrpE.

Figure 5:
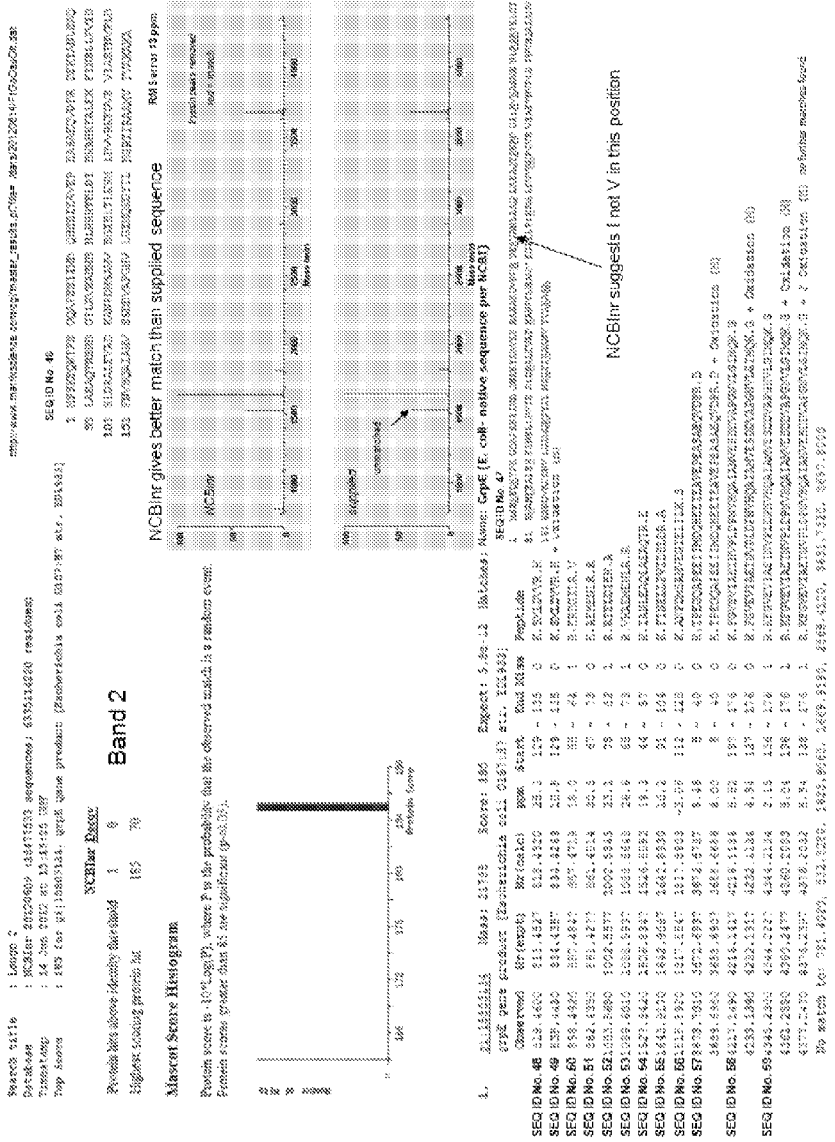
FIG. 5. The MASCOT data of Band 2 shown in FIG. 4 wherein SEQ ID No. 46 is the amino acid sequence of GRPE protein, SEQ ID No. 47 is the amino acid sequence of GRPE protein suggested by NCBInr, and SEQ ID Nos. 48-59 are the MASCOT peptide fragments of GRPE protein.

Based on the MASCOT results, the partial protein sequence is depicted in FIG. 5.

Figure 6:
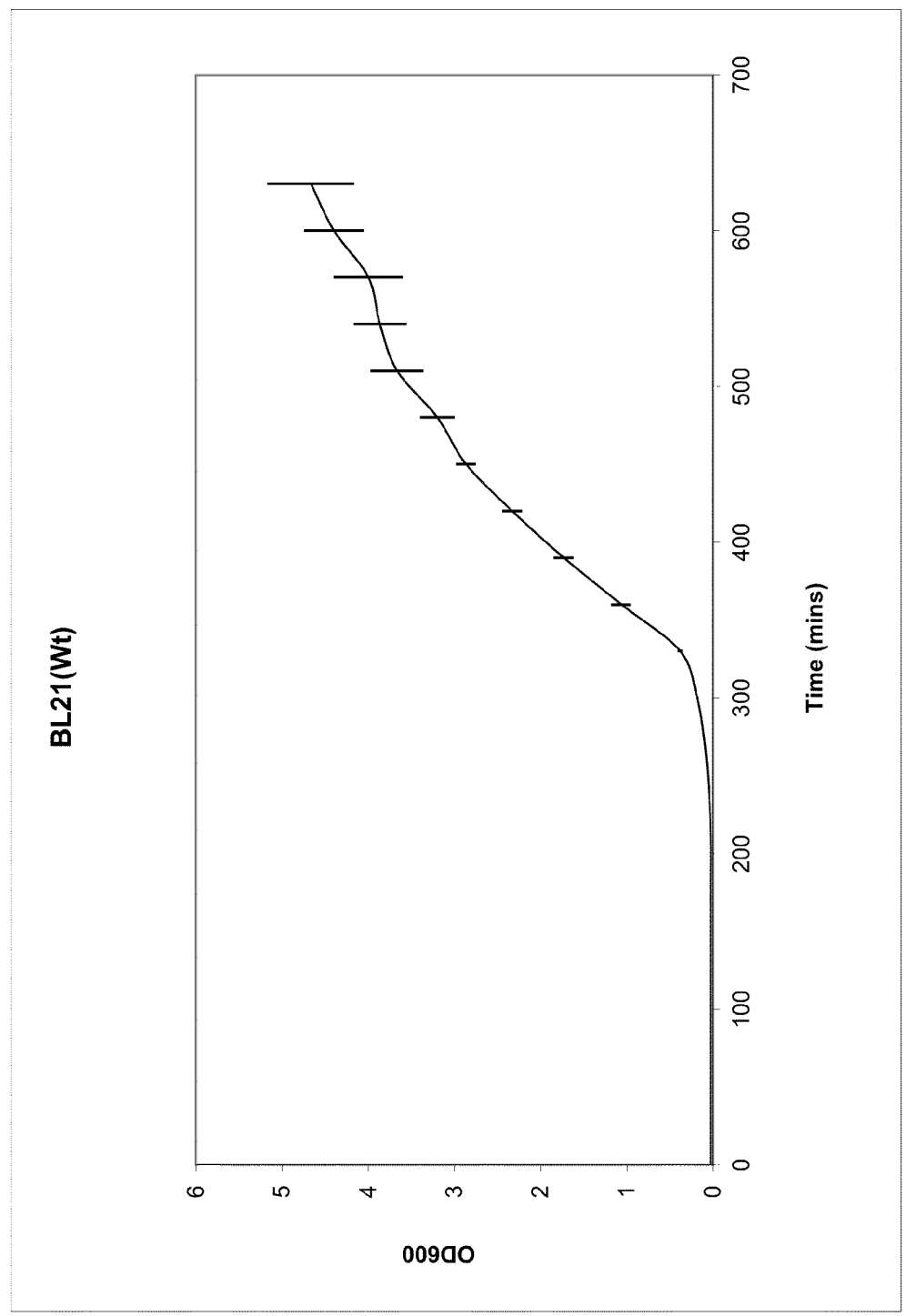
FIG. 6. The growth curve of wild type BL21 strain.
Figure 7:
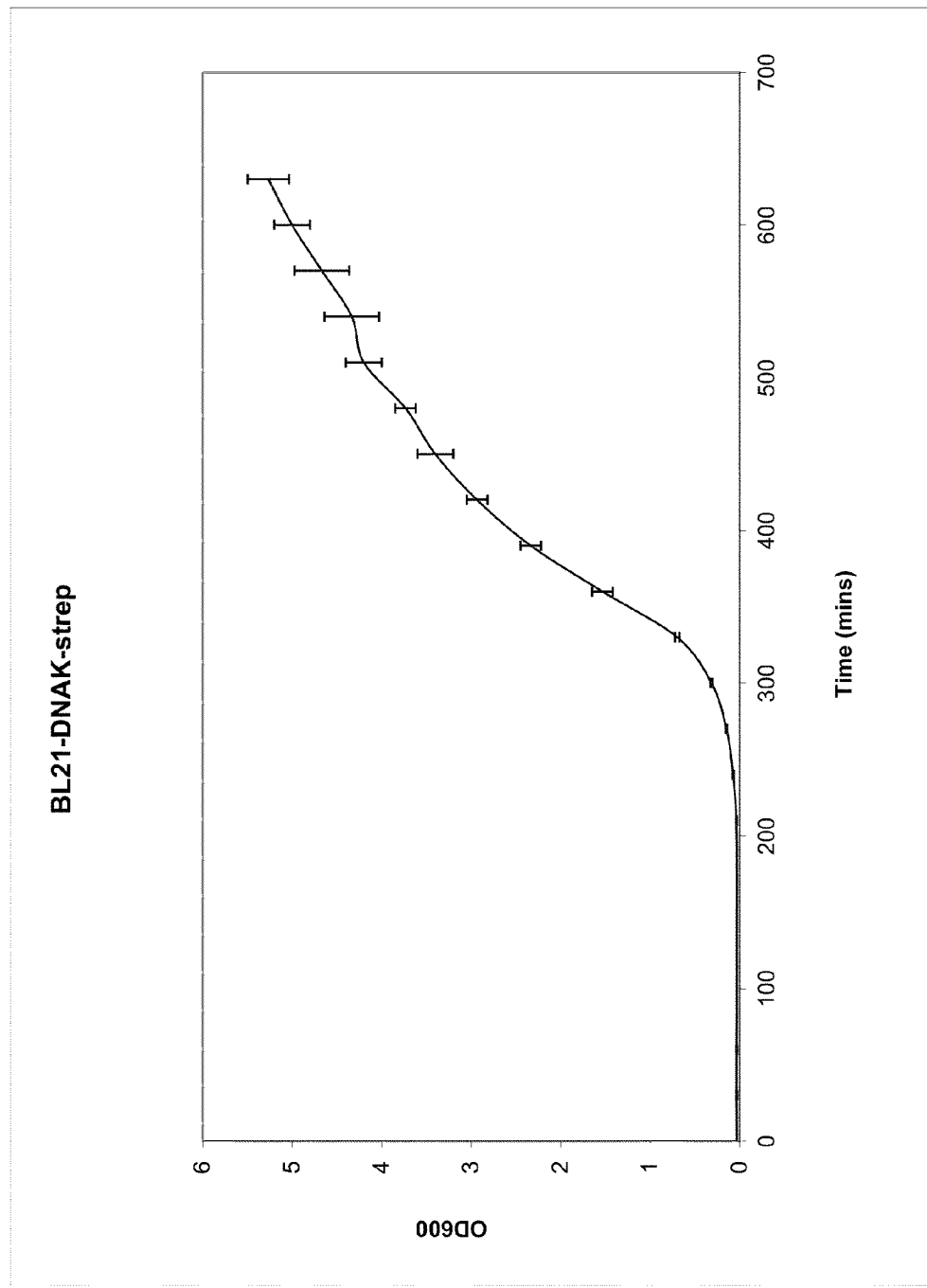
FIG. 7. The growth curve of the BL21 DNAK STREP strain.

With regards to studying bacterial strains of endogeneous proteins, the present invention would not sacrifice bacterial viability and growth. In the exemplary modified strain, the resultant modified strain may then be monitored to growth. In the exemplary embodiment the modified strain, BL21-DNAK Strep strain and the wild-type BL21 (DE3) strain were separately inoculated into LB media and growth was observed over 630 minutes (10.5 hours) which is consistent with the mid-log phase growth. Mid-log phase growth is the optimal for growth phase when expressing recombinant protein in bacteria. See FIGS. 6 & 7. Growth curves demonstrated that there was no substantial difference bacterial growth over this period.

Protein level expression remains unaffected by the presence of the tagged DNAK given that the functionality of DNAK is still able to functionally interact with GrpE as shown in FIG. 1. DNAK removal is also far superior than previous methods used to remove DNAK. In the exemplary embodiment, a BL21-DNAK strain transformed with recombinant protein vector that ultimately expresses a 30 kDa and 36 kDa monomer proteins and the strain was grown to mid-log phase. The cell lysate was isolated and applied to a size exclusion column (SEC) as shown in FIG. 1.A. The recombinant protein found in fractions corresponding to the hydrodynamic molecular weight range of the native recombinant protein were collected and run on an SDS-PAGE with the earliest collected fraction in lane 1. The DNAK band was observed around 72 kDa.

SEC fractions from lane 2-8 were pooled and applied to a gravity flow Strep-tactin resin column. FIG. 2.B shows an aliquot of the lanes for the input sample (lane 1) and the elute fractions (lanes 2-5) which were eluted by 2.5 mM D-Desthiobtion. The tagged DNAK protein was the only protein to visibly remain with no detectable presence of the 30 kDa or 36 kDa recombinant protein.

FIG. 1.C shows the pooled flow fraction from the Strep-tactin resin column used for FIG. 1.B which was reapplied to an SEC. The contaminating tagged DNAK was significantly removed with minimal loss of the recombinant protein. FIG. 1D shows that there are still traces amounts of bound protein coupled with the tagged DNAK.

(iii) Uses

The present invention provides a crucial solution to the problem of reducing DNAK contamination of another targeted isolated protein without affecting the viability of the bacteria, optimal protein production levels, and the proper folding and formation of the expressed recombinant protein. The present invention also does not require the use of reagents that are costly or prohibited for recombinant sample that would be used for commercial or therapeutic applications.

A recognizable tag may be inserted into any region of the DNAK sequence that does not significantly impair the function of DNAK as well as bacterial growth. However, tags that do partially impair DNAK function may be used for recombinant proteins that have a weak affinity for DNAK.

The tag may be a protein tag and may be, but not limited to a Strep-, Myc-, His-, or Flag tag. Multiple tags may be added to DNAK to enhance the selective and isolation.

The tag may also be a recognizable ribonucleic acid tag wherein expression of DNAK may be stopped at the RNA level by factors that recognize the tag and inhibit translation. Such a tag may provide another means of inhibiting DNAK production during the varying growth phases of the bacteria.

While one of the exemplary embodiments of the present invention utilize a BL21 strain, any bacterial strain and its chromosomal DNAK gene may be modified as provided in this present invention.

The present invention may be used to replace DNAK homologs or other chaperone proteins present in eukaryotic cells such as yeast or mammalian cells or cell lines. Such application may improve commercial applications for recombinant protein expression that require post translational modifications.

In the present invention, a tagged DNAK bacterial strain may be transformed with the vector of the target recombinant protein. After the transformed bacterial culture has been incubated to the optimal level of growth, the cellular extract may be collected by standard means of isolation known to those with ordinary skill in the art. The cellular lysates may then be applied to isolation method that targets the tag of the tagged DNAK protein. Such methods include solid phase support isolation such as chromatography or resins attached to tubes or equivalent solid supports. In the alternate liquid phase separation may be employed. An example of a liquid phase separation may involve a magnetic bead that is attached to a ligand that may be bound by the tag that is attached to the DNAK.

In alternate methods, tagged DNAK may be removed after the target recombinant protein has been initially isolated. Other methods may include subsequent rounds of tagged DNAK isolation.

The use of this bacterial strain will also save cost on expensive purification procedures. Recombinant protein expression and isolation is one of the most widely used methods in research and commercial industry. Reagents such as ATP and glycerol can be eliminated. In addition, having endogeneous DNAK tag strains reduces the need to transform bacterial strains with a plasmid into DNAK deletion strains resulting in greater consistency in experimental results as well as a reduction in cost and time.

The elimination for the need of a DNAK tag plasmid also reduces the chance that the recombinant proteins plasmid or the DNAK tag plasmid is lost during bacterial growth.

DNAK tag bacterial strains may be used to produce recombinant proteins for therapeutic use where the chances of immune responses stemming from DNAK or DNAK bound proteins other than the recombinant protein are eliminated or lowered. In addition, the use of the inventive strain reduces the need for use of reagents that may have a toxic effect if present in medicinal preparation of the isolated recombinant protein.

Tagged DNAK may be also be used when a particular protein that is known to bind to DNAK may be isolated when the particular protein is expressed and isolated from DNAK tag strains. This may be useful for both diagnostic and research applications.

Tagged DNAK amino acid sequence could also be modified with protease sensitive recognition sites and such recognition sites may be employed to along with the tagged DNAK to further decrease any trace amounts of DNAK.

While the specification describes particular embodiments of the present invention, those of ordinary skill can devise variations of the present invention without departing from the inventive concept.

What is claimed is:

1. A bacteria comprising:
a first nucleic acid sequence that encodes for at least nucleotides 630 to 2334 of SEQ ID No: 1 and a first tag; and the first tag's nucleic acid sequence does not encode for a 6-His tag; and wherein the first tag's nucleic acid sequence was inserted after nucleotide number 2334 of SEQ ID No: 1.

2. The bacteria of claim 1 wherein a linker nucleic acid sequence is inserted between the nucleotide nucleic acid sequence that encodes for at least nucleotides 630 to 2334 of SEQ ID NO: 1 and the tag.

3. The bacteria of claim 1 wherein an endogenous nucleic acid sequence of DNAK was deleted.

4. The bacteria of claim 1 wherein an endogenous nucleic acid sequence of DNAK was genetically altered to reduce expression of the endogenous nucleic acid sequence of DNAK.

5. The bacteria of claim 1 wherein the first nucleic acid is located on a bacterial chromosome.

6. The first nucleic acid of claim 5 is comprised of at least part of the endogenous nucleic acid sequence that encodes for a DNAK protein.

7. The bacteria of claim 1 wherein the bacteria has a second nucleic acid that is not endogenous and has been genetically altered to encode for a second protein and a second tag, and the second tag is different from the first tag.

8. A bacteria comprising:
a genetically altered first nucleic acid that encodes for at least nucleotides 630 to 2334 of SEQ ID No: 1 and a first tag, wherein the first tag's nucleic acid sequence was inserted after nucleotide number 2334 of SEQ ID No: 1; and a second nucleic acid that does not exist in nature that encodes for a second protein and a second tag, wherein the first tag and the second tag are not the same; and wherein the DNAK protein and the second protein do not substantially interact with each other.

\* \* \* \* \*